United States Patent
Bonningue et al.

(10) Patent No.: US 7,427,262 B2
(45) Date of Patent: Sep. 23, 2008

(54) ENDOSCOPE WITH DEFLECTED DISTAL VIEWING

(75) Inventors: Isabelle Bonningue, Soisy sur Seine (FR); John Le Quellec, Vaux le Penil (FR); Jean Rovegno, La Ciotat (FR)

(73) Assignee: SNECMA, Paris (FR)

( * ) Notice: Subject to any disclaimer, the term of this patent is extended or adjusted under 35 U.S.C. 154(b) by 403 days.

(21) Appl. No.: 10/961,021

(22) Filed: Oct. 12, 2004

(65) Prior Publication Data

US 2005/0085698 A1    Apr. 21, 2005

(30) Foreign Application Priority Data

Oct. 16, 2003    (FR) .................................. 03 12063

(51) Int. Cl.
  *A61B 1/00*    (2006.01)
  *A61B 1/04*    (2006.01)
  *A61B 1/06*    (2006.01)

(52) U.S. Cl. .......................... 600/173; 600/129; 600/170

(58) Field of Classification Search ................ 600/111, 600/129, 166, 170–171, 174–177, 173; 348/65–67
  See application file for complete search history.

(56) References Cited

U.S. PATENT DOCUMENTS

| | | | |
|---|---|---|---|
| 3,456,641 A | 7/1969 | Yokota et al. | |
| 3,818,902 A * | 6/1974 | Kinoshita et al. | 600/109 |
| 4,195,904 A | 4/1980 | Yamashita | |
| 4,224,929 A * | 9/1980 | Furihata | 600/116 |
| 4,273,110 A | 6/1981 | Groux | |
| 4,628,207 A | 12/1986 | Elfert et al. | |
| 4,699,463 A * | 10/1987 | D'Amelio et al. | 385/118 |
| 4,727,859 A * | 3/1988 | Lia | 356/241.5 |
| 4,784,118 A * | 11/1988 | Fantone et al. | 600/160 |
| 4,784,135 A | 11/1988 | Blum et al. | |
| 5,014,709 A | 5/1991 | Bjelkhagen et al. | |
| 5,115,136 A | 5/1992 | Tomasch | |
| 5,170,775 A | 12/1992 | Tagami | |
| 5,486,641 A | 1/1996 | Shum et al. | |
| 5,881,195 A | 3/1999 | Walker | |
| 6,400,980 B1 | 6/2002 | Lemelson | |
| 6,537,209 B1 * | 3/2003 | Pinkhasik et al. | 600/170 |
| 6,560,013 B1 | 5/2003 | Ramsbottom | |
| 6,638,216 B1 * | 10/2003 | Durell | 600/173 |
| 6,876,446 B2 | 4/2005 | Taylor et al. | |
| 2003/0187325 A1 * | 10/2003 | Meister et al. | 600/108 |

(Continued)

FOREIGN PATENT DOCUMENTS

DE    29 17 436    11/1980

(Continued)

*Primary Examiner*—John P. Leubecker
*Assistant Examiner*—Philip R Smith
(74) *Attorney, Agent, or Firm*—Oblon, Spivak, McClelland, Maier & Neustadt, P.C.

(57) ABSTRACT

An endoscope with deflected distal viewing, comprises a rigid tube containing observation means, themselves comprising a distal deflector prism having a viewing axis that is inclined relative to the axis of the tube, and ultraviolet light guide means housed in the tube and opening out at their distal end onto a prism for deflecting the illuminating light beam in a direction that is substantially parallel to the viewing axis. The invention applies in particular to inspecting parts by the penetration test technique in the aviation field.

17 Claims, 2 Drawing Sheets

U.S. PATENT DOCUMENTS

2003/0229270 A1 * 12/2003 Suzuki et al. ............... 600/178
2005/0200842 A1    9/2005 Bonningue et al.

FOREIGN PATENT DOCUMENTS

| | | |
|---|---|---|
| DE | 195 12 518 | 10/1995 |
| JP | 49-89989 | 8/1974 |
| JP | 56-119224 | 9/1981 |
| JP | 57-200125 | 12/1982 |
| JP | 59-22201 | 5/1984 |
| JP | 63-249104 | 10/1988 |
| JP | 05-232387 | 9/1993 |
| JP | 07-005377 | 1/1995 |
| JP | 09-138358 | 5/1997 |
| JP | 52-65086 | 5/1997 |
| JP | 11-113842 | 4/1999 |
| JP | 2001-299940 | 10/2001 |
| JP | 2003-180617 | 7/2003 |

* cited by examiner

ENDOSCOPE WITH DEFLECTED DISTAL VIEWING

The invention relates to an endoscope with ultraviolet illumination and with deflected distal viewing intended in particular for observing defects presented by mechanical parts and shown up by using penetration test substances.

The invention applies particularly, but not exclusively, to industrial endoscopy, in particular in the field of aviation, for visually inspecting internal parts that are difficult to access, such as, for example, the rotor blades of a turbojet or turboprop, by means of an endoscope which is caused to pass through an orifice of small diameter (e.g. 9 millimeters (mm)) which is provided for this purpose in the casing of the machine to be inspected, this technique presenting the advantage of not requiring total or partial prior disassembly of the machine.

BACKGROUND OF THE INVENTION

Endoscopes are known which are constituted essentially by a rigid probe for insertion into a dark cavity and fitted with means for illuminating an object to be inspected and with optical means for providing the user with an image of the object. In general, the optical means comprise a distal objective lens for forming an image, an image transmission means formed by a series of lenses, and a proximal eyepiece lens which can be moved longitudinally to adjust the focus of the image observed by the user. The optical means are preferably designed in such a manner that the image transmitted through the eyepiece lens is not inverted relative to reality. The lighting means generally comprise a bundle of optical fibers having a distal end located close to the distal objective lens in order to illuminate the object, the bundle of fibers being connected at its proximal end to a light source.

Axial-viewing endoscopes exist in which the optical axis of the distal objective lens coincides with the longitudinal axis of the endoscope. The lighting means of such endoscopes are constituted by a bundle of optical fibers having a distal end that generally forms a illuminating ring around the distal objective lens.

Endoscopes are also known with deflected viewing, in which the optical viewing axis is inclined relative to the longitudinal axis of the endoscope. The optical observation means of such an endoscope comprise a distal deflecting prism which is generally a prism that reflects the image unidirectionally, where such a prism is generally referred to as a "partial reflection prism". Under such circumstances, the image transmission means mounted in the endoscope generally include a proximal correcting prism which rectifies the inverted image supplied by the distal deflecting prism.

The lighting means of an endoscope with deflected distal viewing are generally constituted by a bundle of optical fibers having a distal end with a bend so as to constitute a lateral lighting window between the distal deflecting prism and the distal end of the endoscope, with the lighting axis being substantially parallel to the viewing axis.

The lighting optical fibers are glass fibers capable of transmitting the spectral components of white light as applied by a light source such as a quartz iodine lamp or a xenon lamp, without significant attenuation of the light. Such lighting means are unsuitable for transmitting ultraviolet light as produced, for example, by a mercury vapor lamp; and in order to transmit ultraviolet radiation it is necessary to use fibers made of quartz or of a suitable plastics material, or indeed a liquid conductor (a sheath filled with an appropriate liquid that is transparent to ultraviolet radiation), such light conductors possessing a degree of rigidity and not enabling their distal ends to be bent with a radius of curvature that is small enough to enable them to be mounted in an endoscope.

In the prior art, this problem has been solved by associating an axial viewing endoscope with an ultraviolet light conductor and a distal endpiece including a deflector mirror. However that solution is not very satisfactory because of the limited optical field and because of the degradation over time of the efficiency with which ultraviolet light is reflected by the mirror, dirt and mirror defects leading to losses of energy that do not enable an object to be illuminated with sufficient intensity and which impede observation by returning a fuzzy image of the illuminated object.

OBJECTS AND SUMMARY OF THE INVENTION

A particular object of the invention is to provide a solution to these problems that is simple, effective, and inexpensive.

The invention provides an endoscope with ultraviolet illumination and with deflected distal viewing that does not present the above-mentioned drawbacks.

To this end, the invention provides an endoscope with deflected distal viewing, the endoscope comprising a rigid tube containing lighting means and observation means comprising deflector prisms mounted at the distal end of the tube, light guide means extending substantially from one end of the tube to the other as far as the deflector prism of the lighting means, and image transmission means extending from the deflector prism of the observation means to a proximal end of the tube, wherein the two deflector prisms of the lighting means and of the observation means are disposed transversely side by side in the tube and oriented to deflect the illumination light beam supplied by the guide means in a direction that is substantially parallel to the viewing axis of the prism of the observation means.

The transverse disposition of the two prisms side by side is compact and makes the endoscope easier to use.

According to another characteristic of the invention, the light guide means are ultraviolet light guide means and open out longitudinally at the distal end of the tube onto the deflector prism of the lighting means.

This makes it possible to use light guide means which are not angled or bent.

According to another characteristic of the invention, the two prisms are fixedly mounted on a common cradle capable of pivoting about a transverse axis carried by the endoscope, said axis being perpendicular or substantially perpendicular to the viewing axis and the lighting axis.

Advantageously, the endoscope includes means for controlling pivoting of the cradle from the proximal end of the tube.

This makes it possible to view forwards, sideways, or backwards, and to improve the conditions which objects for inspection can be observed.

According to yet another characteristic of the invention, a screen that is opaque to ultraviolet radiation is mounted between the two prisms, in order to prevent parasitic illumination light from being picked up directly by the observation means, said opaque screen being fixed on or formed by the cradle carrying the two prisms, for example.

It is also possible to make provision in the endoscope of the invention for the viewing axis and the lighting axis to converge substantially at a determined lateral distance from the endoscope tube in order to achieve better lighting and better observation of objects situated at said distance.

BRIEF DESCRIPTION OF THE DRAWINGS

The invention will be better understood and other characteristics, details, and advantages thereof will appear more clearly on reading the following description, made by way of example and given with reference to the accompanying drawings, in which.

MORE DETAILED DESCRIPTION

Figure 1:
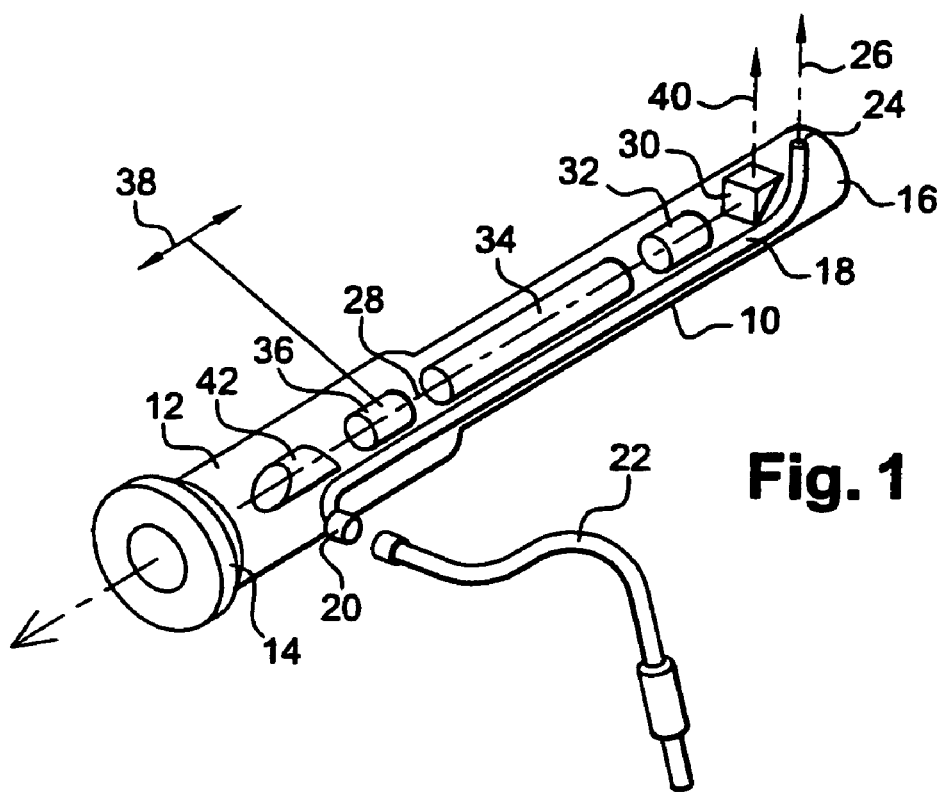
FIG. 1 is a diagrammatic perspective view of a prior art endoscope.

Reference is made initially to FIG. 1 which shows a prior art endoscope essentially comprising a rigid rectilinear tube 10 containing lighting means and observation means, the tube 10 having a proximal end forming a handle 12 and provided with an eyepiece cup 14, and a distal end 16 for inserting into a casing, e.g. via a small-diameter orifice therein.

The lighting means housed in the tube 10 comprise a light conductor 18, such as an optical fiber cable, having a proximal end mounted in a connection socket 20 carried by the handle 12 of the endpiece and designed to receive the end of a lighting cable 22 connected to a source of white light. The distal end 24 of the light conductor 18 has a bend, e.g. through substantially a right angle, thereby defining a lighting axis 26 which is inclined relative to the longitudinal axis 28 of the endoscope.

The observation means comprise a viewing prism 30 which is mounted on the longitudinal axis 28 of the endoscope at its distal end, and which is associated with image transmission means housed in the tube 10 on the axis 28 and including an image-forming objective lens 32 and a series of achromatic lenses 34, together with an axially-movable eyepiece lens 36 which serves to adjust the focus of the image by being moved longitudinally 38. The prism 30 defines a viewing axis 40 which is substantially parallel to the lighting axis 26, and is constituted, for example, by a unidirectional reflection prism that produces an inverted image. Under such circumstances, a correcting prism 42 can be mounted on the axis 28 of the endoscope between the lens 36 and the cup 14 in order to rectify the image.

That prior art endoscope enables objects for inspection to be illuminated in white light, but it cannot be used for deflecting defects of the kind shown up by penetration test substances, since that requires the defects to be illuminated in ultraviolet light.

Figure 2:
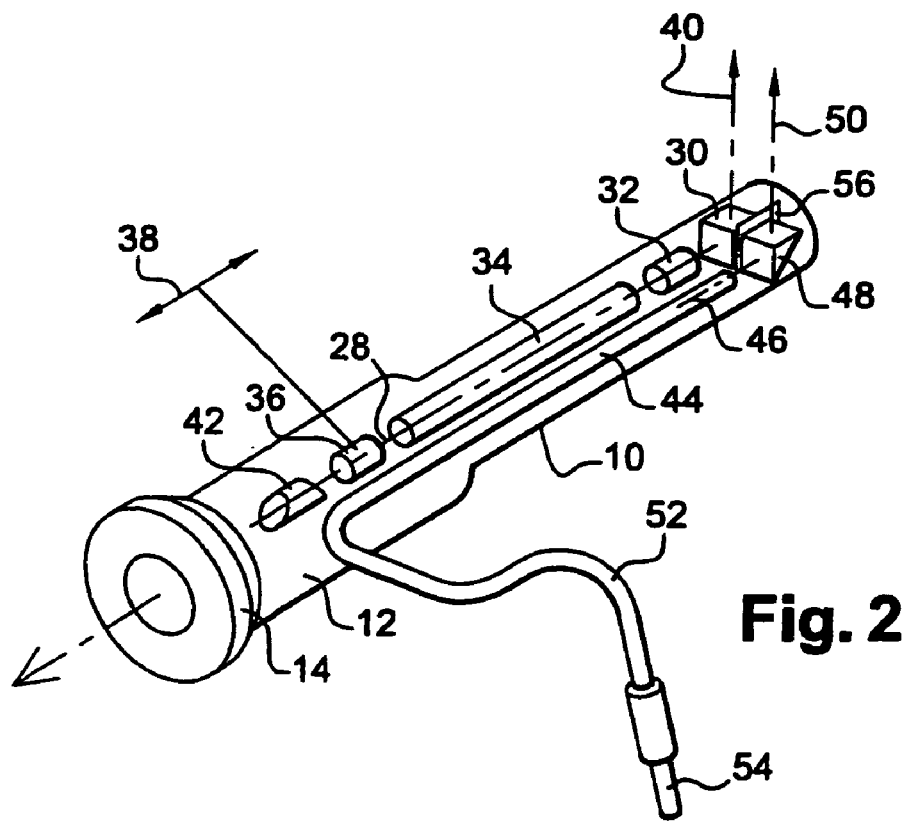
FIG. 2 is a diagrammatic perspective view of an endoscope of the invention.

Reference is now made to FIG. 2 which is a diagram of an embodiment of an endoscope of the invention.

This endoscope comprises the same rectilinear rigid tube 10 as shown in FIG. 1 and observation means that are similar to those described above, comprising a viewing prism 30 whose viewing axis 40 is inclined relative to the longitudinal axis 28 of the tube 10, an objective lens 32, a series of achromatic lenses 34, an eyepiece lens 36 that is axially movable as shown by arrow 38 in order to adjust the focus of the image, a rectifying prism 42, and a cup 14 mounted at the end of the handle 12 of the endoscope.

The lighting means comprise ultraviolet light guide means 44 contained in the tube 10 and extending along the axis 28, the distal end 46 of the guide means being rectilinear and parallel to the axis 28 so as to lead to a unidirectional reflection prism 48 of the same type as the prism 30 of the observation means, the prism 48 deflecting the ultraviolet light beam coming from the guide means 44 so as to direct said beam in a direction 50 which is substantially parallel to the viewing axis 40.

The proximal end 52 of the light guide means 44 lies outside the endoscope and includes an endpiece 54 for connection to an ultraviolet light source.

Under such circumstances, the ultraviolet light guide means 44 may be made of quartz fibers, of fibers made of an appropriate plastics material, or a liquid conductor (a sheath filled with an appropriate liquid that is transparent to ultraviolet radiation).

In a variant, the proximal end of the ultraviolet light guide means 44 may be connected to a connection socket carried by the handle 12 of the endoscope, as in the endoscope of FIG. 1, and an ultraviolet light conducting cable provided with a suitable endpiece can be connected to the socket. The light guide means 44 are preferably made of quartz fibers and the external cable is preferably a liquid cable.

The lighting prism 48 is made of quartz or of a glass that is transparent to ultraviolet radiation and thus transmits with very good efficiency (e.g. greater than 99%) the ultraviolet light delivered by the external source.

In all cases, the source of ultraviolet light connected to the guide means 44 includes a bandpass filter centered on the ultraviolet wavelength required by the user of the endoscope.

The prisms 30 and 48 are mounted in the immediate vicinity of the distal end of the tube 10, as close as possible to said end, and a screen 56 that is opaque to ultraviolet radiation is mounted between the two prisms so as to avoid any parasitic ingress of ultraviolet light into the prisms 30, the objective lens 32, and the lenses 34 of the observation means.

Figure 3:
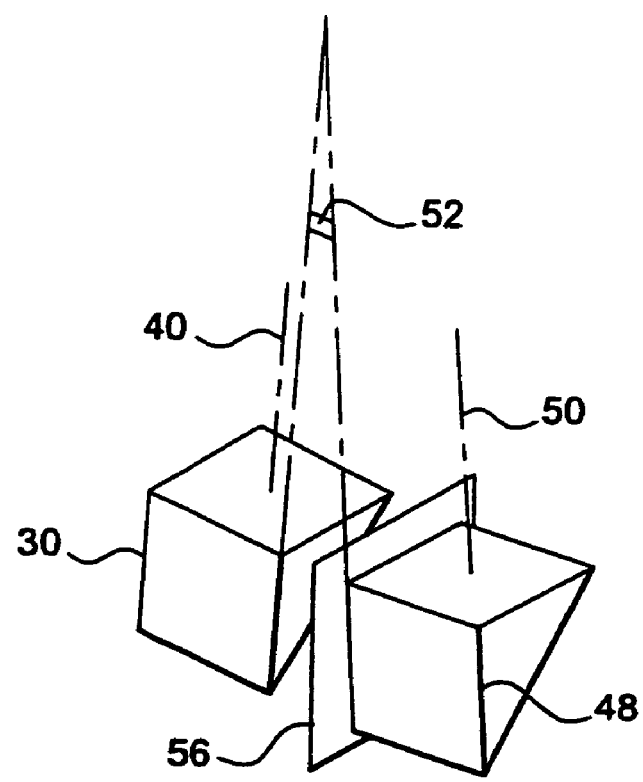
FIG. 3 is a fragmentary view showing a particular way of mounting the prisms of the endoscope of the invention.

As shown diagrammatically in FIG. 3, at least one of the prisms 30, 48 is tilted laterally towards the other prism so that the viewing axis 40 and the lighting axis 50 converge, at least approximately, at a certain distance from the endoscope, forming between them a small angle 52. This improves the lighting and the observation of objects that are situated at a radial distance from the endoscope corresponding approximately to the distance at which the axes 40 and 50 converge.

The orientations of these axes relative to the longitudinal axis 28 of the endoscope can be fixed and predetermined, with viewing being in a forward direction (relative to the endoscope), a sideways direction (at about 90° to the longitudinal axis 28), or in a rearward direction (looking towards the back of the endoscope).

Figure 4:
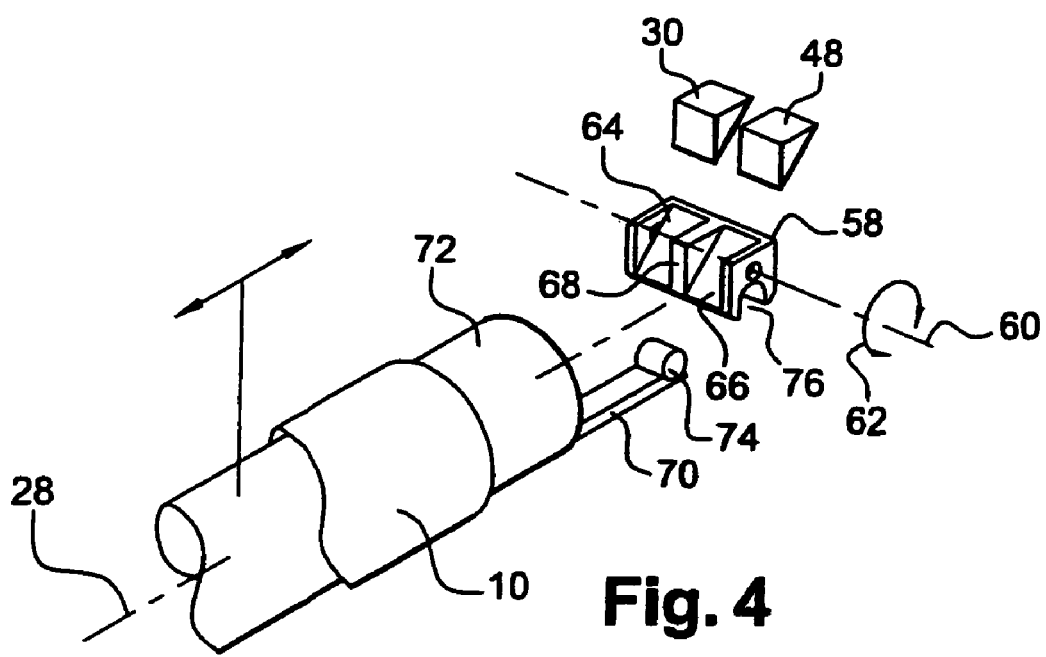
FIG. 4 is an exploded diagrammatic perspective view showing how the prisms of the endoscope of the invention are mounted to pivot.

In a variant, and as shown diagrammatically in FIG. 4, the prisms 30 and 48 may be mounted on a common cradle 58, which is itself mounted to pivot about a transverse axis 60 as represented by double-headed arrow 62, the transverse axis 60 being perpendicular to the longitudinal axis 28 of the endoscope and perpendicular or substantially perpendicular to the viewing and lighting axes 40 and 50, these axes being parallel or else converging as shown in FIG. 3.

The cradle 58 may include two housings 64, 66 intended respectively to receive the prism 30 and to receive the prism 48, these housings being separated by an intermediate partition 68 forming a screen between the two prisms.

The pivot axis 60 of the cradle 58 is embodied by any appropriate means, for example two diametrally-opposite studs carried by the distal end of the tube 10 and engaging in two orifices in the cradle.

Advantageously, means are provided to cause the cradle 58 to pivot about the axis 60 under control from the proximal end of the endoscope, these means comprising, for example, a longitudinal tab 70 whose distal end is hinged to the cradle 58 about an axis parallel to the axis 60, and whose proximal end is secured to a tube 72 that is slidably mounted inside the tube 10 of the endoscope, the proximal end of the tube 72 being movable in axial translation by the user.

By way of example, the distal end of the tab 70 comprises a transverse cylindrical finger 74 received in a transverse semicylindrical recess 76 in the bottom portion of the cradle 58.

This enables the user to pivot the cradle 58 about the axis 60 and thus to steer the viewing axis 40 and the lighting axis 50 about said axis in order to view forwards, sideways, or backwards.

What is claimed is:

1. An endoscope with deflected distal viewing, the endoscope comprising:
   a rigid tube containing lighting means and observation means, said lighting means comprising a first single deflector prism mounted at the distal end of the tube and defining a lighting axis, said observation means comprising a second single deflector prism mounted at the distal end of the tube and defining a viewing axis,
   light guide means extending substantially from a proximal end of the tube to the deflector prism of the lighting means, and
   image transmission means extending from the deflector prism of the observation means to the proximal end of the tube,
   wherein the first and second deflector prisms are disposed transversely side by side and are carried by a common cradle configured to pivot about a transverse axis perpendicular or substantially perpendicular to the viewing axis or the lighting axis, at least one of the deflector prisms being tilted laterally towards the other prism so that the viewing axis and the lighting axis converge at a certain distance from the endoscope,
   further comprising a longitudinal tab hinged to said cradle about a hinge axis substantially parallel to said transverse axis at a distal end of said longitudinal tab,
   wherein a proximal end of said longitudinal tab is secured to an adjusting tube, said adjusting tube being slidably mounted inside said rigid tube, and
   wherein said distal end of said longitudinal tab comprises a transverse cylindrical finger received in a transverse semi-cylindrical recess in a bottom portion of the cradle.

2. An endoscope according to claim 1, wherein the light guide means are ultraviolet light guide means and open out longitudinally at the distal end of the tube onto the deflector prism of the lighting means.

3. An endoscope according to claim 2, wherein the ultraviolet light guide means comprise a cable of quartz fibers, or a cable of fibers made of an appropriate plastics material, or a leakproof sheath filled with an appropriate liquid.

4. An endoscope according to claim 2, wherein the ultraviolet light guide means include a proximal end outside the tube and provided with an endpiece for connection to an ultraviolet light source.

5. An endoscope according to claim 2, wherein the ultraviolet light guide means have a proximal end mounted in a socket secured to the tube and suitable for being connected to a light conductor external to tube.

6. An endoscope according to claim 5, wherein the light conductor external to the tube is a sheath filled with an appropriate liquid.

7. An endoscope according to claim 1, wherein the image transmission means comprise an objective lens and a series of achromatic lenses together with a proximal correcting prism for rectifying the inverted image supplied by the distal prism.

8. An endoscope according to claim 1, including means for controlling pivoting of the cradle from the proximal end of the tube.

9. An endoscope according to claim 1, wherein a screen that is opaque to ultraviolet radiation is mounted between the two deflector prisms.

10. An endoscope according to claim 9, wherein the screen is carried by or formed by the cradle carrying the prisms.

11. An endoscope according to claim 1, wherein the first deflector prism of the lighting means is made of quartz or of a glass that is transparent to ultraviolet radiation.

12. An endoscope according to claim 1, wherein said transverse axis is substantially perpendicular to a longitudinal axis of said tube.

13. An endoscope according to claim 1, wherein said viewing axis is substantially parallel to said lighting axis.

14. An endoscope according to claim 1, wherein said cradle includes two housings that respectively receive said first single deflector prism and said second single deflector prism.

15. An endoscope according to claim 14, wherein said two housings are separated by an intermediate partition that forms a screen between said first single deflector prism and said second single deflector prism.

16. An endoscope according to claim 1, wherein said common cradle includes a screening portion that prevents parasitic illumination light from the lighting means from being picked up by the observation means.

17. An endoscope with deflected distal viewing, the endoscope comprising:
   a rigid tube containing lighting means and observation means, said lighting means comprising a first single deflector prism mounted at the distal end of the tube and defining a lighting axis, said observation means comprising a second single deflector prism mounted at the distal end of the tube and defining a viewing axis,
   light guide means extending substantially from a proximal end of the tube to the deflector prism of the lighting means,
   image transmission means extending from the deflector prism of the observation means to the proximal end of the tube,
   a longitudinal tab hinged to said cradle about a hinge axis substantially parallel to said transverse axis at a distal end of said longitudinal tab,
   wherein the first and second deflector prisms are disposed transversely side by side and are carried by a common cradle configured to pivot about a transverse axis perpendicular or substantially perpendicular to the viewing axis or the lighting axis,
   wherein a proximal end of said longitudinal tab is secured to an adjusting tube, said adjusting tube being slidably mounted inside said rigid tube, and
   wherein said distal end of said longitudinal tab comprises a transverse cylindrical finger received in a transverse semi-cylindrical recess in a bottom portion of the cradle.

\* \* \* \* \*